US007704723B2

(12) United States Patent
Huhnke et al.

(10) Patent No.: US 7,704,723 B2
(45) Date of Patent: Apr. 27, 2010

(54) ISOLATION AND CHARACTERIZATION OF NOVEL CLOSTRIDIAL SPECIES

(75) Inventors: Raymond L. Huhnke, Stillwater, OK (US); Randy S. Lewis, Provo, UT (US); Ralph S. Tanner, Norman, OK (US)

(73) Assignees: The Board of Regents For Oklahoma State University, Stillwater, OK (US); The Board of Regents of the University of Oklahoma, Norman, OK (US)

( * ) Notice: Subject to any disclaimer, the term of this patent is extended or adjusted under 35 U.S.C. 154(b) by 320 days.

(21) Appl. No.: 11/514,385

(22) Filed: Aug. 31, 2006

(65) Prior Publication Data

US 2008/0057554 A1    Mar. 6, 2008

(51) Int. Cl.
*C12N 1/20* (2006.01)
*C12M 1/04* (2006.01)

(52) U.S. Cl. .................. 435/252.1; 435/161; 435/289.1; 435/303.2

(58) Field of Classification Search ........................ None
See application file for complete search history.

(56) References Cited

U.S. PATENT DOCUMENTS

| | | | |
|---|---|---|---|
| 4,292,406 | A | 9/1981 | Ljungdahl et al. |
| 4,568,644 | A | 2/1986 | Wang et al. |
| 5,173,429 | A | 12/1992 | Gaddy et al. |
| 5,192,673 | A | 3/1993 | Jain et al. |
| 5,593,886 | A | 1/1997 | Gaddy |
| 5,807,722 | A | 9/1998 | Gaddy |
| 5,821,111 | A | 10/1998 | Grady et al. |
| 5,932,456 | A | 8/1999 | Van Draanen et al. |
| 6,136,577 | A | 10/2000 | Gaddy |
| 6,340,581 | B1 | 1/2002 | Gaddy |
| 6,368,819 | B1 | 4/2002 | Gaddy et al. |
| 6,753,170 | B2 | 6/2004 | Gaddy et al. |
| 2007/0275447 | A1 | 11/2007 | Lewis et al. |

OTHER PUBLICATIONS

Liou, S., J.E. McGuire, and R.S. Tanner. 2002. Conversion of synthesis gas to ethanol by clostridial strain P7. Abst. Ann. Meet. Am. Soc. Microbiol., O10, p. 348.*
Saxena, J., and R.S. Tanner. 2006. Effect of trace metals on ethanol production by *Clostridium* strain P11. Abst. Ann. Meet. Am. Soc. Microbiol., O6, p. 422.*
Bahl et al.., "Nutrititional Factors Affecting the Ratio of Solvents Products by *Clostridium acetobutylicum*," *Applied and Environmental Microbiolgy*, 1986, pp. 169-172, vol. 52, No. 1, Publisher: American Society for Microbiology.
Balch et al., "New Approach to the Cultivation of Methanogenic Bacteria: 2-Mercaptoethanesulfonic Acid (HS-CoM)-Dependent Growth of *Methanobacterium ruminatium* in a Pressurized Atmosphere," *Applied and Environmental Microbiology*, 1976, pp. 781-791, vol. 32, No. 6, Publisher: American Society for Microbiology.
Bredwell et al., "Reactor Design Issues for Synthesis-Gas Fermentations," *Biotechnol. Prog.*, 1999, pp. 834-844, vol. 15.

Bryant, "Commentary on the Hungate technique for culture of anaerobic bacteria," *The American Journal of Clinical Nutrition*, 1972, pp. 1324-1328, vol. 25.
Buschhorn et al., "Production and Utilization of Ethanol by the Homoacetogen *Acetobacterium woodii*," *Applied and Environmental Microbiology*, 1989, pp. 1835-1840, vol. 55, No. 7, Publisher: American Society for Microbiology.
Collins et al., "The Phylogeny of the Genus *Clostridium*: Proposal of Five New Genera and Eleven New Species Combinations," *International Journal of Systemacit Bacteriology*, 1994, pp. 812-826, vol. 44, No. 4, Publisher: International Union of Microbiological Societies.
Johnson et al., "Taxonomy of the Clostridia: Ribosomal Ribonucleic Acid Homologies among the Species," *Journal of General Microbiology*, 1975, pp. 229-244, vol. 88.
Mesbah et al., "Precise Measurement of the G+C Content of Deoxyribonucleic Acid by High-Performance Liquid Chromatography," *International Journal of Systematic Bacteriology*, 1989, pp. 159-167, vol. 39, No. 2, Publisher: International Microbiological Societies.
T.B. Reed, Editor, *Biomass Gasification Principles and Technology*, 1981, Publisher: Noyes Data Corporation, Published in: Park Ridge, NJ, USA.
Rothstein, "*Clostridium thermosaccharolyticum* Strain Deficient in Acetate Production," *Journal of Bacteriology*, 1986, pp. 319-320, vol. 165, No. 1, Publisher: Americal Society for Microbiology.
Wayne et al., "Report of the Ad Hoc Committee on Reocnciliation of Approaches to Bacterial Systematics," *International Journal of Systematic Bacteriology*, 1987, pp. 463-464, vol. 37, No. 4, Publisher: International Union of Microbiological Societies. Yomano et al., "Isolation and characterization of ethanol-tolerant mutants of *Escherichia coli* KO11 for fuel ethanol production," *Journal of Industrial Microbiology & Biotechnology*, 1998, pp. 132-138, vol. 20, Publisher: Society for Industrial Microbiology.
U.S. Appl. No. 11/514,385, Not Yet Published, Huhnke et al.
Liou et al., Production of Acids and Alcohols From Co by Clostridial Strain P7, Abst. Ann. Meet. Am. Soc. Microbiol., O11, 2001, p. 533.
Rajagopalan et al., Synthesis Gas Conversion to Ethanol, AlChE Annual Meeting, Nov. 12-17, 2000.
Liou et al., Conversion of Synthesis Gas to Ethanol by Clostridial Strain P7, Abst. Ann. Meet. Am. Soc. Microbiol., O10, 2002, p. 348.
Liou et al., *Clostridium carboxidivorans* sp. Nov., A Solvent-Producing *Clostridium* Isolated From an Agricultural Settling Lagoon, and, Reclassification of the Acetogen *Clostridium scatologenes* Strain SL1 as *Clostridium drakei* sp. Nov. International Journal of Systematic & Evolutionary Microbiology, 2005, pp. 2085-2091, vol. 55, Published in: UK.
Gaddy et al., Production of Ethanol From Biomass by Gasification/Fermentation, American Chemical Soceity, Jan. 1, 1993.

(Continued)

*Primary Examiner*—Irene Marx
(74) *Attorney, Agent, or Firm*—Fellers, Snider, Blankenship, Bailey & Tippens

(57) ABSTRACT

A novel clostridia bacterial species (*Clostridium ragsdalei*, ATCC BAA-622, "P11") is provided. P11 is capable of synthesizing, from waste gases, products which are useful as biofuel. In particular, P11 can convert CO to ethanol. Thus, this novel bacterium transforms waste gases (e.g. syngas and refinery wastes) into useful products. P11 also catalyzes the production of acetate.

5 Claims, 5 Drawing Sheets

OTHER PUBLICATIONS

Tanner, et al., *Clostridium ljungdahlii* sp. Nov., An Acetogenic Species in Clostridial rRNA Homology Group I, *International Journal of Systematic Bacteriology*, 1993, pp. 232-236, vol. 43, No. 2, Publisher: International Union of Microbiological Societies, Published in: US.

Ntis, Bench-Scale Demonstration of Biological Production of Ethanol From Coal Synthesis Gas, Jul. 1, 1994, Published in: US.

Michigan Biotechnology Institute, Bioconversion of Coal Derived Synthesis Gas to Liquid Fuels, *Quarterly Technical Progress Report*, Oct. 14, 1994, pp. 1-8, Publisher: Michigan Biotechnology Institute, Published in: US.

Barik, et al, Biological Production of Ethanol From Coal Synthesis, *Biorpocessing and Biotreatment of Coal*, 1990, pp. 131-154, Publisher: Marcel Dekker, Inc., Published in: US.

Klasson, et al, Bioreactor Design for Synthesis Gas Fermentations, Fuel, 1991, pp. 605-614, vol. 70, Publisher: Butterworth-Heinmann, Ltd., Published in: US.

Abrini, et al., *Clostridium autoethanogenum*, sp. Nov., An Anaerobic Bacterium That Produces Ethanol From Carbon Monoxide, *Microbiology*, 1994, pp. 345-351, vol. 161, Publisher: Arch Microbial, Published in: Belgium.

Arora, et al, Production of Ethanol From Refinery Waste Gases, Phase II Technology Development Annual Report, Jul. 1995, pp. 1-56, Publisher: National Technical Information Service, Published in: US.

Michigan Biotechnology Institute, Bioconversion of Coal Derived Synthesis Gas to Liquid Fuels, Quarterly Technical Progress Report, Oct. 25, 1993, pp. 1-9, Publisher: Michigan Biotechnology Institute, Published in: US.

Michigan Biotechnology Institute, Bioconversion of Coal Derived Synthesis Gas to Liquid Fuels, Quarterly Technical Progress Report, Jan. 16, 1995, Publisher: Michigan Biotechnology Institute, Published in: US.

Vega, et al, Design of Bioreactors for Coal Synthesis Gas Fermentations, *Resources, Conservation and Recycling*, Jul. 16, 1989, pp. 149-160, vol. 3, Publisher: Elsevier Science Publishers, Published in: The Netherlands.

University of Arkansas, High Pressure Synthesis Gas Conversion, May 1993, Publisher: National Technical Information Service, Published in: US.

Phillips, et al., Synthesis Gas as Substrate for the Biological Production of Fuels and Chemicals, *Applied Biochemistry and Biotechnology*, 1994, pp. 145-156, vol. 45, Publisher: Humana Press, Published in: US.

PCT Search Report for PCT/US07/77264, Sep. 26, 2008.

Drake, Harold L., "Acetogenesis, Acetogenic Bacteria, and the Acetyl-CoA 'Wood/Ljungdahl' Pathway: Past and Current Perspectives", Acetogenesis, 1994, Page(s) Chapter 1, Publisher: Chapman Hall, Published in: New York.

Tanner, Ralph S., "Cultivation of Bacteria and Fungi", Chapter 6 of Manual of Environmental Microbiology Third Edition, 2007, pp. 69-78, Publisher: American Society for Microbiology.

Tumbula, D.L. et al., "Long-Term Maintenance of Methanogen Stock Cultures in Glycerol", Protocol 8 of Archaea a Laboratory Manual, 1995, Publisher: Cold Spring Harbor Laboratory Press.

Versalovic, James, et al., "Genomic Fingerprinting of Bacteria Using Repetitive Sequence-Based Polymerase Chain Reaction", Methods in Molecular and Cellular Biology, 1994, pp. 25-40, vol. 5, Publisher: Wiley-Liss, Inc.

Wiegel, Juergen, et al., "An Introduction to the Family *Clostridiaceae*", Prokaryotes, 2006, pp. 654-678, vol. 4.

Dubois et al., "Colorimetric Method for Determination of Sugars and Related Substances," *Anal. Chem.*, 1956, pp. 350-356, vol. 28.

Grethlein et al., "Continuous Production of Mixed Alcohols and Acids from Carbon Monoxide," *Applied Biochemistry and Biotechnology*, 1990, pp. 875-884, vol. 24, No. 25, Publisher: The Humana Press, Inc.

Johnson, "Similarity Analysis of DNAs," *Methods for General and Molecular Microbiology*, 1994, pp. 665-682, Publisher: American Society for Microbiology.

Smibert et al., "Phenotypic Characterization," *Methods for General and Molecular Microbiology*, 1994, pp. 611-654, Publisher: American Society for Microbiology.

Tanner, "Cultivation of Bacteria and Fungi," *Manual of Environmental Microbiology*, 1997, pp. 52-60, Publisher: ASM Press.

Tanner, "Cultivation of Bacteria and Fungi," *Manual of Environmental Microbiology 2nd Edition*, 2002, pp. 62-70, Publisher: American Society for Microbiology.

Zeikus, "Chemical and Fuel Production by Anaerobic Bacteria," *Annu. Rev. Microbiol.*, 1980, pp. 432-464, vol. 34, Publisher: Annual Reviews, Inc.

Ahmed et al., Effects of Biomass-Generated Syngas Constituents on Cell Growth, Product Distribution and Hydrogenase Activity of *Clostridium carboxidivorans* P7 The 2005 Annual Meeting (Cincinnati, OH), Nov. 2, 2005, # 303f.

Lewis et al. Abstracts of Papers, 227th ACS National Meeting, Anaheim, CA, United States, Mar. 28-Apr. 1, 2004., CELL-115 Publisher: American Chemical Society, Washington, D.C.

Datar, Rohit, et al., "Fermentation of Biomass-Generated Producer Gas to Ethanol", "Biotechnology and Bioengineering", Apr. 15, 2004, pp. 587-594, vol. 86, No. 5, Publisher: Wiley Periodicals, Inc., Published in: US.

* cited by examiner

- Clostridium novyi L37594
- Clostridium tetanomorphum X68184
- Clostridium pascui X96736
- Clostridium algidicarnis
- Clostridium barati M59102
- Clostridium paraputrificum X73445
- Clostridium cellulovorans
- Clostridium butyricum M59085
- Clostridium pasteurianum M23930
- Clostridium ljungdahlii M59097
- P11
- Clostridium tyrobutyricum M59113
- Clostridium magnum X77835
- Clostridium scatologenes M59104
- Clostridium putrificum X73442
- Clostridium sporogenes X68189
- Clostridium limosum M59096
- Clostridium histolyticum M59094
- Clostridium proteolyticum X73448

FIG. 4

ISOLATION AND CHARACTERIZATION OF NOVEL CLOSTRIDIAL SPECIES

STATEMENT REGARDING FEDERALLY SPONSORED RESEARCH OR DEVELOPMENT

This invention was made using funds from grants from the United States Department of Agriculture Cooperative State Research, Education and Extension Service having grant numbers 2001-34447-10302, 2002-34447-11908, 2003-34447-13162, 2004-34447-14487, 2005-34447-15711. The United States government may have certain rights in this invention.

BACKGROUND OF THE INVENTION

1. Field of the Invention

The invention generally relates to bacteria that are capable of producing biofuel from waste. In particular, the invention provides a novel clostridial species (*Clostridium ragsdalei*) having the identifying characteristics of ATCC No. BAA-622) and a method of synthesizing ethanol and other useful products from CO using the clostridia species.

2. Background of the Invention

It was not until the petroleum crises of the 1970's that the U.S. government started funding more initiatives to find a way to develop renewable resources to alleviate the country's dependence on oil imports (Klass, 1998). It was also then when the government had a renewed interest in biobased solvent production for gasoline blending. One of particular interest and even more so recently, is bioethanol (ethanol from biomass).

Currently the major mode of bioethanol production is through direct fermentation, which accounts for 90% of the ethanol output in the U.S. (Licht, 2001). Direct fermentation is the process in which a saccharolytic microorganism, such as a yeast or bacteria, converts sugars to ethanol. These sugars may be simple (i.e. glucose) or complex (i.e. starch, cellulose, hemicellulose). Corn starch is the primary substrate used in ethanol producing plants today. Other than corn starch, lignocellulosic biomass (i.e. grasses, small trees, paper waste, saw dust) is also being researched as a substrate for this process. Lignocellulose is comprised of cellulose, hemicellulose, pectin, and lignin. The difficulty with the direct fermentation of lignocellulosic biomass is that added pretreatment processes are necessary to break down the biomass into its individual components before microorganismal utilization. This adds more cost in the areas of materials, plant design, waste management, etc In an attempt to make the most out the resources available for the production of fuel ethanol, alternative methods are being examined. One of these alternative methods is indirect fermentation. Indirect fermentation is the process in which lignocellulosic biomass is pyrolyzed (burned to produce gases) and the gases produced are converted to ethanol by bacteria. The gases produced are generally termed synthesis gas. Synthesis gas ($C—H_2—CO_2$), a product of pyrolyzed biomass or coal, has been and is currently being recognized for its potential role in the indirect fermentation of biomass to fuel alcohol (Zeikus, 1980, Bredwell et. al., 1980).

Anaerobic microorganisms such as acetogenic bacteria offer a viable route to convert syngas to useful products, in particular to liquid biofuels such as ethanol. Such bacteria catalyze the conversion of syngas with higher specificity, higher yields and lower energy costs than can be attained using chemical processes (Vega et al, 1990; Phillips et al., 1994). Several microorganisms capable of producing biofuels from waste gases and other substrates have been identified:

Three strains of acetogens (Drake, 1994) have been described for use in the production of liquid fuels from syngas: *Butyribacterium methylotrophicum* (Grethlein et al., 1990; Jain et al., 1994b); *Clostridium autoethanogenum* (Abrini et al., 1994); *Clostridium ljungdahlii* (Arora et al, 1995; Barik et al., 1988; Barik et al. 1990; and Tanner et al., 1993). Of these, *Clostridium ljungdahlii* and *Clostridium autoethanogenum* are known to convert CO to ethanol.

U.S. Pat. No. 5,173,429 to Gaddy et al. discloses *Clostridium ljungdahlii* ATCC No. 49587, an anaerobic microorganism that produces ethanol and acetate from CO and $H_2O$ and/or $CO_2$ and $H_2$ in synthesis gas.

U.S. Pat. No. 5,192,673 to Jain et al. discloses a mutant strain of *Clostridium acetobytylicum* and a process for making butanol with the strain.

U.S. Pat. No. 5,593,886 to Gaddy et al. discloses *Clostridium ljungdahlii* ATCC No. 55380. This microorganism can anaerobically produce acetate and ethanol using waste gas (e.g. carbon black waste gas) as a substrate.

U.S. Pat. No. 5,807,722 to Gaddy et al. discloses a method and apparatus for converting waste gases into useful products such as organic acids and alcohols using anaerobic bacteria, such as *Clostridium ljungdahlii* ATCC No. 55380.

U.S. Pat. No. 6,136,577 to Gaddy et al. discloses a method and apparatus for converting waste gases into useful products such as organic acids and alcohols (particularly ethanol) using anaerobic bacteria, such as *Clostridium ljungdahlii* ATCC Nos. 55988 and 55989.

U.S. Pat. No. 6,136,577 to Gaddy et al. discloses a method and apparatus for converting waste gases into useful products such as organic acids and alcohols (particularly acetic acid) using anaerobic strains of *Clostridium ljungdahlii*.

U.S. Pat. No. 6,753,170 to Gaddy et al. discloses an anaerobic microbial fermentation process for the production of acetic acid.

Other strains of aceotgens have also been described for use in the production of liquid fuels from synthesis gas, e.g.: *Butyribacterium methylotrophicum* (Grethlein et al., 1990, Appl. Biochem. Biotech. 24/24:875-884); and *Clostridium autoethanogenum* (Abrini et al., 1994, Arch. Microbiol. 161: 345-351).

There remains an ongoing need to discover and develop additional microorganisms that are capable of producing useful products such as biofuels via fermentation. In particular, it would be advantageous to provide microbes that are robust, relatively easy to culture and maintain, and that provide good yields of products of interest, such as biofuels.

SUMMARY OF THE INVENTION

The present invention provides a novel biologically pure anaerobic bacterium (*Clostridium ragsdalei*, American Type Culture Collection Accession No. BAA-622, (now PTA-7826) deposited at the American Type Culture Collection located at 10801 University Blvd. in Manassas, Va., on October [provide calendar day] 2002, also referred to as "P11") that is capable of producing high yields of valuable organic fluids from relatively common substrates. In particular, the microorganism can produce ethanol and acetic acid by fermenting CO. One common source of CO is syngas, the gaseous byproduct of coal gasification. The microbes can thus convert substances that would otherwise be waste products into valuable products, some of which are biofuels. Syngas, and thus CO, can also be produced from readily available low-cost agricultural raw materials by pyrolysis, providing a means to address both economic and environmental concerns of energy production. The bacteria of the invention thus participate in the indirect conversion of biomass to biofuel via a gasification/fermentation pathway.

Cultures of *Clostridium ragsdalei* are extremely stable and can be stored on the at room temperature or in a 38° C. incubator for over one year while retaining activity.

It is an object of this invention to provide a biologically pure culture of the microorganism *Clostridium ragsdalei*. The microorganism has all of the identifying characteristics of ATCC No. BAA-622. In addition, the invention provides a composition for producing ethanol. The composition comprises 1) a source of CO, and 2) *Clostridium ragsdalei*. In one embodiment of the invention, the source of CO is syngas.

In yet another embodiment, the invention provides a method of producing ethanol. The method comprises the step of combining a source of CO and *Clostridium ragsdalei* under conditions which allow said *Clostridium ragsdalei* to convert CO to ethanol.

The invention further provides a system for producing ethanol, the system comprising 1) a vessel in which a source of CO is combined with *Clostridium ragsdalei*; and 2) a controller which controls conditions in said vessel which permit the *Clostridium ragsdalei* to convert the CO to ethanol. In one embodiment of the invention, the system also includes 1) a second vessel for producing syngas; and 2) a transport for transporting the syngas to the vessel, wherein the syngas serves as the source of CO. Such a system is illustrated in FIG. 5, which shows the vessel 100 and controller 101, with the optional second vessel 200 and transport 201.

BRIEF DESCRIPTION OF THE DRAWINGS

FIG. 4. Phylogenetic tree based on 16S rDNA gene sequence similarities and constructed using the neighbor-joining method, indicating the position of *C. ragsdalei* ATCC BAA-622 and representative species of the genus of *Clostridium*. GenBank accession numbers for the 16s rRNA sequences are given after the strain numbers.

DETAILED DESCRIPTION OF THE PREFERRED EMBODIMENTS OF THE INVENTION

Figure 1:
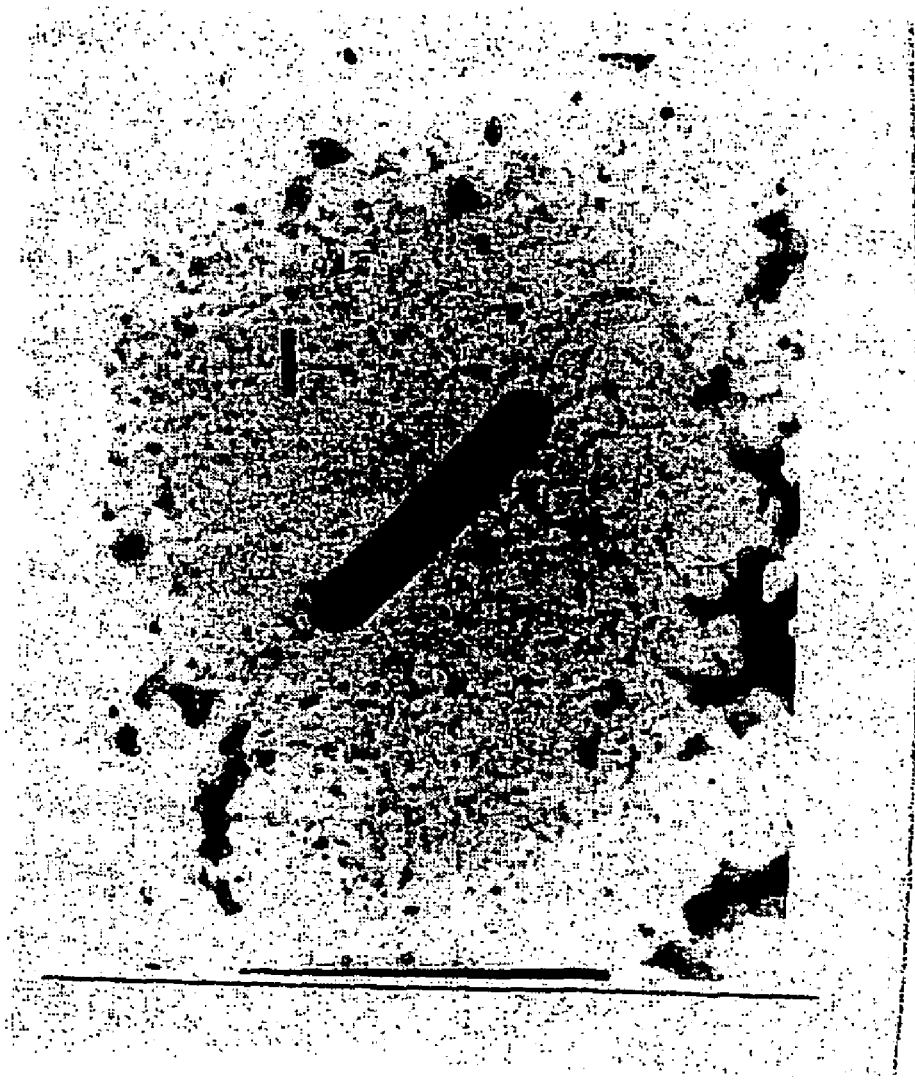
FIG. 1. Transmission electron micrograph of negatively stained cell of strain P11. Bar, 1 μm.

The present invention is based on the discovery of a novel acetogenic bacterium that is capable, under anaerobic conditions, of producing high yields of valuable products from CO and other readily available substrates. In particular, the microorganism produces valuable liquid products such as ethanol, butanol and acetate by fermenting CO, with ethanol being a predominant product. By "fermenting" we mean a physiological process whereby the substrate serves as both the source of electrons and the electron sink (oxidation of a portion of the substrate and reduction of a portion of the substrate) which can be used for the production of products such as alcohols and acids. As a result, this organism is capable of converting what would otherwise be waste gases into useful products such as biofuel. The anaerobic microbe of the invention is a novel clostridia species which displays the characteristics of purified cultures represented by ATCC deposit BAA-622, herein referred to as "P11".

The morphological and biochemical properties of P11 have been analyzed and are described herein in the Examples section below. While certain of the properties of P11 are similar to other *Clostridium* species, P11 possesses unique characteristics that indicate it is a novel species of this genus. P11 has been denominated *Clostridium ragsdalei*, and is considered to be representative of this species.

The bacteria in the biologically pure cultures of the present invention have the ability, under anaerobic conditions, to produce ethanol from the substrates $CO+H_2O$ and/or $H_2+CO_2$ according to the following reactions:

Ethanol Synthesis

$$6CO+3H_2O \rightarrow C_2H_5OH+4CO_2 \quad (1)$$

$$6H2+2CO_2 \rightarrow C_2H_5OH+3H_2O \quad (2)$$

With respect to the source of these substrates, those of skill in the art will recognize that many sources of CO, $CO_2$ and $H_2$ exist. For example, preferred sources of the substrates are "waste" gases such as syngas, oil refinery waste gases, gases (containing some $H_2$) which are produced by yeast fermentation and some clostridial fermentations, gasified cellulosic materials, coal gasification, etc. Alternatively, such gaseous substrates are not necessarily produced as byproducts of other processes, but may be produced specifically for use in the fermentation reactions of the invention, which utilize P11. Those of skill in the art will recognize that any source of substrate gas may be used in the practice of the present invention, so long as it is possible to provide the bacterium with sufficient quantities of the substrate gases under conditions suitable for the microbe to carry out the fermentation reactions. The source of $H_2O$ for the reaction represented by Equation (1) is typically the aqueous media in which the organism is cultured.

In a preferred embodiment of the invention, the source of CO, $CO_2$ and $H_2$ is syngas. Syngas for use as a substrate may be obtained, for example, as a gaseous byproduct of coal gasification. The bacteria thus convert a substance that would otherwise be a waste product into valuable biofuel. Alternatively, syngas can be produced by gasification of readily available low-cost agricultural raw materials expressly for the purpose of bacterial fermentation, thereby providing a route for indirect fermentation of biomass to fuel alcohol. There are numerous examples of raw materials which can be converted to syngas, as most types of vegetation could be used for this purpose. Preferred raw materials include but are not limited to perennial grasses such as switchgrass, crop residues such as corn stover, processing wastes such as sawdust, etc. Those of skill in the art are familiar with the generation of syngas from such starting materials. In general, syngas is generated in a gasifier from dried biomass primarily by pyrolysis, partial oxidation, and steam reforming, the primary products being CO, $H_2$ and $CO_2$. (The terms "gasification" and "pyrolysis" refer to similar processes. Both processes limit the amount of oxygen to which the biomass is exposed. Gasification allows a small amount of oxygen (this may also be referred to as "partial oxidation" and pyrolysis allows more oxygen. The term "gasification" is sometimes used to include both gasification and pyrolysis.) Typically, a part of the product gas is recycled to optimize product yields and minimize residual tar formation. Cracking of unwanted tar and coke in the syngas to CO may be carried our using lime and/or dolomite. These processes are described in detail in, for example, Reed, 1981. (Reed, T. B., 1981, Biomass gasification: principles and technology, Noves Data Corporation, Park Ridge, N.J.)

In addition, combinations of sources of substrate gases may be utilized. For example, the primary source of CO, $CO_2$ and $H_2$ may be syngas, but this may be supplemented with gas from other sources, e.g. from various commercial sources. For example, the reaction according to Equation (1) above generates four molecules of $CO_2$, and reaction according to Equation (2) utilizes 6H2 but only two molecules of $CO_2$. Unless $H_2$ is plentiful, $CO_2$ buildup may occur. However, supplementing the media with additional H2 would result in an increase of the utilization of $CO_2$, and the consequent production of yet more ethanol.

The primary product produced by the fermentation of CO by the bacterium of the present invention is ethanol. However, acetate may also be produced. Acetate production likely occurs via the following reactions:

Acetate Synthesis $$4CO + 2H_2O \rightarrow CH_3COOH + 2CO_2 \quad (3)$$

$$4H_2 + 2CO_2 \rightarrow CH_3COOH + 2H_2O \quad (4)$$

The organisms of the present invention must be cultured under anaerobic conditions. By "anaerobic conditions" we mean that dissolved oxygen is absent from the medium.

In general, the media for culturing the acetogen of the invention is a liquid medium such as ATCC medium 1754 (developed by R. S. Tanner). However, those of skill in the art will recognize that alternative media can be utilized, for example, ATCC medium 1045 under a $H2:CO_2$ or $CO:CO_2$ atmosphere at an initial pH of 6. Further, various media supplements may be added for any of several purposes, e.g. buffering agents, metals, vitamins, salts, etc. In particular, those of skill in the art are familiar with such techniques as nutrient manipulation and adaptation, which result in increased or optimized the yields of a product of interest. For example, culturing microbes under "non-growth" conditions (i.e. conditions which do not favor bacterial growth and reproduction) may result in higher production of fermentation products. This is likely because under non-growth conditions, the resources of the bacteria are not dedicated to reproduction and are therefore free for other synthetic activities. Examples of non-growth conditions include, for example, maintaining the culture at non-optimal temperature or pH, the limitation of nutrients and carbon sources, etc. Generally, non-growth conditions would be implemented after a desired density of bacteria is reached in the culture. Also, it is possible by media optimization to favor production of one product over others, e.g. to favor the production of ethanol over acetate. For example, increasing the concentration of iron tenfold compared to that in standard medium doubles the concentration of ethanol produced, while decreasing the production of acetic acid. Those of skill in the art are familiar with procedures for optimizing the production of desired products, and all such optimized procedures using the P11 bacterium are intended to be encompassed by the present invention. Reference is made, for example, to work carried out with *Clostridium acetobutylicum* which provides guidance for such techniques (see, for example, Bahl et al., 1986, Appl Environ. Microbiol. 52:169-172; and U.S. Pat. No. 5,192,673 to Jain et al. and U.S. Pat. No. 5,173,429 to Gaddy, the complete contents of both of which are hereby incorporated by reference).

In particular, *Clostridium ragsdalei* may be cultured using Balch technique (Balch and Wolfe, 1976, Appl. Environ. Microbiol. 32:781-791; Balch et al., 1979, Microbiol. Rev. 43:260-296), as described in the reviews by: Tanner, 1997, Manual Environ. Microbiol., p. 52-60, ASM Press; Tanner, 2002, Manual Environ. Microbiol. 2nd ed., p. 62-70; Wiegel et al., 2005, An Introduction to the Family Clostridiaceae, The Prokaryotes, Release 3.20; Tanner, 2006, Manual Environ. Microbiol. 3rd ed., ASM Press. This entails the aid of an anaerobic chamber for preparing culture materials and a gas exchange manifold to establish whatever gas phase is desired for culture in sealed tubes or vessels. More specific details on culturing solvent-producing acetogens, such as the use of an acidic pH, appear in Tanner et al., 1993, Int. J. Syst. Bacteriol. 43:232-236 and Liou et al., 2005, Int. J. Syst. Evol. Microbiol. 55:2085-2091. Methods to enhance ethanol production include optimization of every medium component (such as ammonium, phosphate and trace metals), control of culture pH, mutagenesis and clonal screening etc.

The fermentation of CO by the organisms of the invention can be carried out in any of several types of apparatuses that are known to those of skill in the art, with or without additional modifications, or in other styles of fermentation equipment that are currently under development. Examples include but are not limited to bubble column reactors, two stage bioreactors, trickle bed reactors, membrane reactors, packed bed reactors containing immobilized cells, etc. The chief requirements of such an apparatus include that sterility, anaerobic conditions, and suitable conditions or temperature, pressure, and pH be maintained; and that sufficient quantities of substrates are supplied to the culture; that the products can be readily recovered; etc. The reactor may be, for example, a traditional stirred tank reactor, a column fermenter with immobilized or suspended cells, a continuous flow type reactor, a high pressure reactor, a suspended cell reactor with cell recycle, and other examples as listed above, etc. Further, reactors may be arranged in a series and/or parallel reactor system which contains any of the above-mentioned reactors. For example, multiple reactors can be useful for growing cells under one set of conditions and generating ethanol (or other products) with minimal growth under another set of conditions.

In general, fermentation will be allowed to proceed until a desired level of product is produced, e.g. until a desired quantity of ethanol is produced in the culture media. Typically, this level of ethanol is in the range of at least about 1 gram/liter of culture medium to about 50 gram/liter, with a level of at least about 30 gram/liter (or higher) being preferable. However, cells or cell culturing systems that are optimized to produce from about 1 to 10, or from about 10 to 20, or from about 20 to 30, or from about 30 to 40, or from about 40 to 50 gram/liter are also contemplated. P11 remains viable and will grow in ethanol concentrations of at least 60 g/L. Alternatively, production may be halted when a certain rate of production is achieved, e.g. when the rate of production of a desired product has declined due to, for example, build-up of bacterial waste products, reduction in substrate availability, feedback inhibition by products, reduction in the number of viable bacteria, or for any of several other reasons known to those of skill in the art. In addition, continuous culture techniques exist which allow the continual replenishment of fresh culture medium with concurrent removal of used medium, including any liquid products therein (i.e. the chemostat mode).

The products that are produced by the bacteria of the invention can be removed from the culture and purified by any of several methods that are known to those of skill in the art. For example, ethanol can be removed and further processed, e.g. by solvent extraction; distillation to the azeotrope followed by azeotropic distillation; molecular sieve dehydration; pervaporation; or flow-through zeolite tubes. Those of skill in the art will recognize that the two main techniques in industry for ethanol dehydration following distillation are azeotropic distillation and molecular sieve dehydration. (See, for example, Kohl, S. "Ethanol 101-7: Dehydration" in Ethanol Today, March 2004: 40-41). In addition, depending on the number of products, several separation techniques may need to be employed to obtain several pure products. Likewise, acetate may be removed and further processed by similar processes.

In some embodiments of the invention, P11 is cultured as a pure culture in order to produce ethanol (or other products of interest). However, in other embodiments, P11 may be cultured together with other organisms.

EXAMPLES

Example 1

In an effort to discover novel microbial catalysts capable of efficiently metabolizing syn-gas and producing ethanol, *Clostridium ragsdalei*, a new mesophilic, carbon monoxide utilizing, acetogen was isolated and is described hereafter. The characterization of the new organism was done in part by comparison to known *Clostridium ljundahlii* strain PETC Materials and Methods Organisms. *Clostridium ljundahlii* strain PETC was obtained from a fructose stock culture maintained by Dr. Ralph S. Tanner and was used as the reference control strain. Strain P11 was obtained from an anaerobic enrichment inoculated with fresh water sediment from the Duck Pond at the University of Oklahoma by a procedure described previously (Bryant, 1972) under an atmosphere of $CO:N_2:CO_2$ (75:15:10) and an initial pH of 6.0. The carbon monoxide oxidizing clostridium described within was named *Clostridium ragsdalei*. This bacterium was designated strain P11 and deposited with the American Type Culture Collection as strain ATCC BAA-622.

Media. The medium used in this study was prepared using strict anaerobic technique described by Balch & Wolfe (1976) and contained the mineral salts, trace metals and vitamin solution described by Tanner (2002), supplemented with yeast extract (1 g/L, Difco) (Tables 1-4).

TABLE 1

Mineral stock solution.[a]

| Component | g/liter |
| --- | --- |
| NaCl | 80 |
| $NH_4Cl$ | 100 |
| KCl | 10 |
| $KH_2PO_4$ | 10 |
| $MgSO_4 \cdot 7H_2O$ | 20 |
| $CaCl_2 \cdot 2H_2O$ | 4 |

[a]store at room temperature

TABLE 2

Trace metals solution.[a]

| Component | g/liter |
| --- | --- |
| Nitroloacetic acid | 2.0 |
| Adjust pH to 6 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 0.2 |
| $CuCl_2 \cdot 2H_2O$ | 0.02 |
| $NiCl_2 \cdot 6H_2O$ | 0.02 |
| $Na_2MoO_4 \cdot 2H_2O$ | 0.02 |

TABLE 2-continued

Trace metals solution.[a]

| Component | g/liter |
| --- | --- |
| $Na_2SeO_4$ | 0.02 |
| $Na_2WO_4$ | 0.02 |

[a]Store at 4° C.

TABLE 3

Vitamin solution.[a]

| Component | mg/liter |
| --- | --- |
| Pyridoxine•HCl | 10 |
| Thiamine•HCl | 5 |
| Riboflavin | 5 |
| Calcium pantothenate | 5 |
| Thioctic acid | 5 |
| p-Aminobenzoic acid | 5 |
| Nicotinic acid | 5 |
| Vitamin B12 | 5 |
| MESA[b] | 5 |
| Biotin | 2 |
| Folic acid | 2 |

[a]Store at 4° C. in the dark.
[b]Mercaptoethanesulfonic acid.

TABLE 4

Description of culture medium for strain P11.[a]

| Component | Amount per 1000 mL of $diH_2O$ |
| --- | --- |
| Mineral solution | 25 mL |
| Trace metals solution | 10 mL |
| Vitamin solution | 10 mL |
| Yeast extract | 1.0 g |
| MES[b] | 10 g |
| Reducing agent | 2.0 mL |

[a]pH 6.1-6.3
[b]2-[N-morpholino]ethanesulfonic acid.

Except for the deletion of $NaHCO_3$ and an initial pH 6.3, growth on organic and gaseous substrates was performed as previously described (Tanner et. al., 1993). Resazurin (1 mg/L) was used as the redox indicator. Purified agar was added to the medium at a concentration of 2% for colony morphology description (Table 5). Heat labile substrates were filter sterilized (not autoclaved) and added from sterile stock solutions to a final concentration of 5 g/L before inoculation. The optimum temperature and pH (initial pH) was determined in medium containing fructose as the substrate. For determination of the optimum pH, media was buffered with HOMOPIPES (homopiperazine-N,N'-bis-2-[ethanesulfonic acid] (Research Organics, Cleveland, Ohio), MES (2-[N-morpholino]ethanesulfonic acid), or TES (N-tris [hydroxymethyl]methyl-2-aminoethanesulfonic acid) at (1.0 g/L). A 0.1 ml (~2%) inoculum of fructose-grown cells was used to initiate growth. All media components used in these experiments were obtained from Sigma unless otherwise noted (Sigma Chemical Co., St. Louis, Mo.).

TABLE 5

Nutrient agar used for description of colony morphology.[a]

| Component | Amount per 100 mL diH2O |
|---|---|
| Mineral solution | 2.5 mL |
| Trace metal solution | 1.0 mL |
| Vitamin solution | 1.0 mL |
| Yeast extract | 0.1 g |
| MES[b] | 1.0 g |
| Purified agar (w/v) | 2% |
| Reducing agent | 0.2 mL |

[a]pH 6.1-6.3
[b]Mercaptoethanesulfonic acid.

Biochemical reactions. Biochemical assays for esculin and starch hydrolysis, gelatinase production, and indole production were performed by procedures described by Smibert & Krieg (1994). Nitrate reduction was measured using a CHEMetrics test kit and spectronic 20D set at 520 nm. Cells grown mid to late-exponential phase in medium supplemented with fructose were used for the assays.

Fermentation balance. A fermentation balance was determined for growth on fructose. Fructose was measured using a phenol-sulfuric acid carbohydrate assay (Dubois et. al., 1956). Acetate and ethanol were measured simultaneously by a gas chromatograph (GC) equipped with a flame ionization detector (FID) on a Varian 3400 equipped with a 2 m steel column packed with an 80/120 Carbopak B-DA/4% carbowax resin 20M (Supelco, Bellfonte, Pa.). The column, injector, and detector temperature were 155, 200, and 200° C., respectively. Helium was the carrier gas and flow rate was set at 30 ml min-1. $CO_2$ was measured with a gas chromatograph equipped with a thermal conductivity detector (TCD) (Varian, Sugar Land, Tex.) and a Porapak Super Q 2 m steel column (Alltech, Deerfield, Mich.). The column temperature was set at 60° C. with a flow rate of 15 ml min-1 and helium as the carrier gas.

Electron and phase contrast microscopy. Exponential-phase cells grown on 0.5% yeast extract as substrate were used for transmission electron microscopy. Cells were spread onto carbon coated Formvar grids, fixed with 1% glutaraldehyde, and stained with 0.5% phosphotunsgate (pH 7.0). Cells were examined and photographed using a JEOL JEM 2000 FX TEM. An Olympus CH-2 phase-contrast microscope was used to observe cells.

Analytical methods. Growth was measured spectrophotometrically at 600 nm (Spectronic 20D; Milton Roy) in aluminum seal tubes (Balch & Wolfe, 1976). To demonstrate strain P11 was capable of utilizing a substrate, growth had to occur after consecutive transfers in replicate tubes. For the substrate malate, utilization was analyzed by HPLC ("high-performance liquid chromatography") equipped with a UV detector set at 214 nm using a Alltech, Prevail Organic Acid column (4.6×150 mm, 5 μm; Alltech, Deerfield, Mich.) with a mobile phase of 25 mM $KH_2PO_4$, pH 2.5 and 10% (v/v) methanol.

DNA for mol % G+C (guanine plus cytosine) analysis was isolated according to a modified method of the Marmur procedure (Johnson, 1994) and included treatments with lysozyme, proteinase K and RNase. A lysozyme treatment of at least 6 hours was found to be most effective. The G+C content was measured by HPLC (Mesbah et al., 1989). An Alltech, Prevail C18 reversed-phase column (4.6×250 mm, 5 μm particle size; Alltech, Deerfield, Ill.) was used with a mobile phase of 25 mM $KH_2PO_4$, pH 2.5 and 4% (v/v) acetonitrile, and a UV detector set at 254 nm.

BOX-PCR genomic fingerprinting. Repetitive DNA PCR fingerprinting was performed using the BOXAIR primer, obtained from Invitrogen (Carlsbad, Calif.) and the protocol from Versalovic et al. (1994). PCR mixtures contained 2.5 μl 10× buffer B (500 mM KCl and 100 mM Tris.HCl, Fisher Scientific), 2 μl $MgCl_2.6H_2O$ (25 mM, Fisher Scientific), 0.25 μl Taq polymerase (Fisher Scientific), 0.5 μl of each deoxynucleoside triphosphate (10 mM, Promega, Madison, Wis.), 1 μl primer, and sample DNA in a final volume of 25 μl. The PCR reaction was run on a Robocycler Gradient 40 Temperature Cycler (Stratagene, Cedar Creek, Tex.) using a protocol of an initial denaturation step (94° C., four min, one cycle), 30 reaction cycles (94° C. for one min, 50° C. for one min, 72° C. for eight min), and a final extension step (72° C. for eight min). PCR product (10 μl) was run on a 5% polyacrylamide vertical gel with a 100 base pair ladder (Fisher Scientific) for 17 hr at 26° C. and 120 mAmps. The ethidium bromide-stained gel image was analyzed using a NucleoCam Digital Image Documentation System (Nucleo Tech Corp., San Mateo, Calif.). 16S rDNA sequence analysis. The sequence analysis was performed according to the procedures described by Chandler et al. (1997).

DNA hybridization. The DNA hybridization assays were performed at the DSMZ using the previously described methods of Wayne et al. (1987).

Nucleotide sequence analysis. The GenBank accession numbers for the 16s rDNA gene sequences of strain P11 ATCC BAA-622 are AY1700378 and DQ20022.

Results and Discussion

Cellular morphology. Cells of strain P11 were rarely motile, rod-shaped, stained gram-positive, and occurred singly or in chains. Cells were 0.7-0.8 μm by 4-5 μm and were peritrichously flagellated (see FIG. 1). Spores occurred infrequently, but when present were non-swelling and located subterminal to terminal. Colonies appeared circular, translucent and flat on nutrient agar.

Physiology. *Clostridium ragsdalei* was strictly anaerobic. Yeast extract stimulated growth, although in its absence marginal growth was observed after an extended lag phase. Autotrophic growth occurred with $H_2/CO_2$ or $CO/CO_2$ and chemoorganotrophic growth was observed with the following substrates: pyruvate, D-threose, xylose, mannose, fructose, glucose, sucrose, ethanol, 1-propanol, casamino acids, glutamate, serine, choline, and alanine (Table 6). Malate or formate did not initially support growth even when examined at a pH range of 5.0-6.5. However, after an incubation period of about thirty days in the tested pH range *C. ljungdahlii* was able to grow with malate as the sole carbon source. This is indicative that this organism may require adaptation to malate under the conditions tested. Similar requirements have been shown with *C. ljungdahlii* when grown on glucose. Table 6 shows a comparison between strain P11 and *Clostridium ljungdahlii* strain PETC and their growth on substrates as sole carbon and energy sources.

TABLE 6

Comparison of substrate utilization by *Clostridium ragsdalei* strain P11 and *Clostridium ljundahlii* strain PETC

| Substrate | C. ragsdalei | C. ljungdahlii |
|---|---|---|
| $H_2/CO_2$ | + | + |
| CO | + | + |
| Na-Formate | − | − |
| Na-Acetate | − | − |
| Na-Lactate | − | − |

TABLE 6-continued

Comparison of substrate utilization by *Clostridium ragsdalei* strain P11 and *Clostridium ljundahlii* strain PETC

| Substrate | *C. ragsdalei* | *C. ljungdahlii* |
|---|---|---|
| Glycolic acid | − | − |
| Na-Pyruvate | + | + |
| Na-Propionate | − | − |
| Na-Succinate | − | − |
| Na-Citrate | − | +* |
| Malic acid | − | − |
| Na-Fumarate | − | −* |
| Maleic acid | − | − |
| Gluconic acid | − | +† |
| Lactose | − | − |
| D (−) Threose | + | + |
| L (+) Threose | − | − |
| Erythrose | − | − |
| Arabinose | − | −* |
| Xylose | + | + |
| Mannose | + | + |
| Fructose | + | + |
| Glucose | + | + |
| Sucrose | + | +* |
| Fucose | − | − |
| Rhamnose | − | +† |
| Galactose | − | − |
| Maltose | − | − |
| Melibiose | − | − |
| Melizitose | − | − |
| Trehalose | − | − |
| Turanose | − | − |
| Methanol | − | − |
| Ethanol | + | + |
| Iso-propanol | − | − |
| 1-Propanol | + | +† |
| Butanol | − | +† |
| Glycerol | − | − |
| Mannitol | − | − |
| Sorbitol | − | − |
| Inositol | − | − |
| Cellibiose | − | − |
| Inulin | − | − |
| Amygdalin | − | − |
| Salicin | − | − |
| Cellulose | − | − |
| Starch | − | − |
| Glycogen | − | − |
| Pectin | − | − |
| Trimethoxybenzoic acid | − | − |

TABLE 6-continued

Comparison of substrate utilization by *Clostridium ragsdalei* strain P11 and *Clostridium ljundahlii* strain PETC

| Substrate | *C. ragsdalei* | *C. ljungdahlii* |
|---|---|---|
| alpha-ketoglutarate | − | + |
| Amino Acids | | |
| Casamino acids | + | + |
| Arginine | − | + |
| Glutamate | + | +† |
| Histidine | − | +† |
| Glutamine | − | − |
| Serine | + | +† |
| Choline | + | +† |
| Betaine | − | − |
| Alanine | + | +* |

Figure 2:
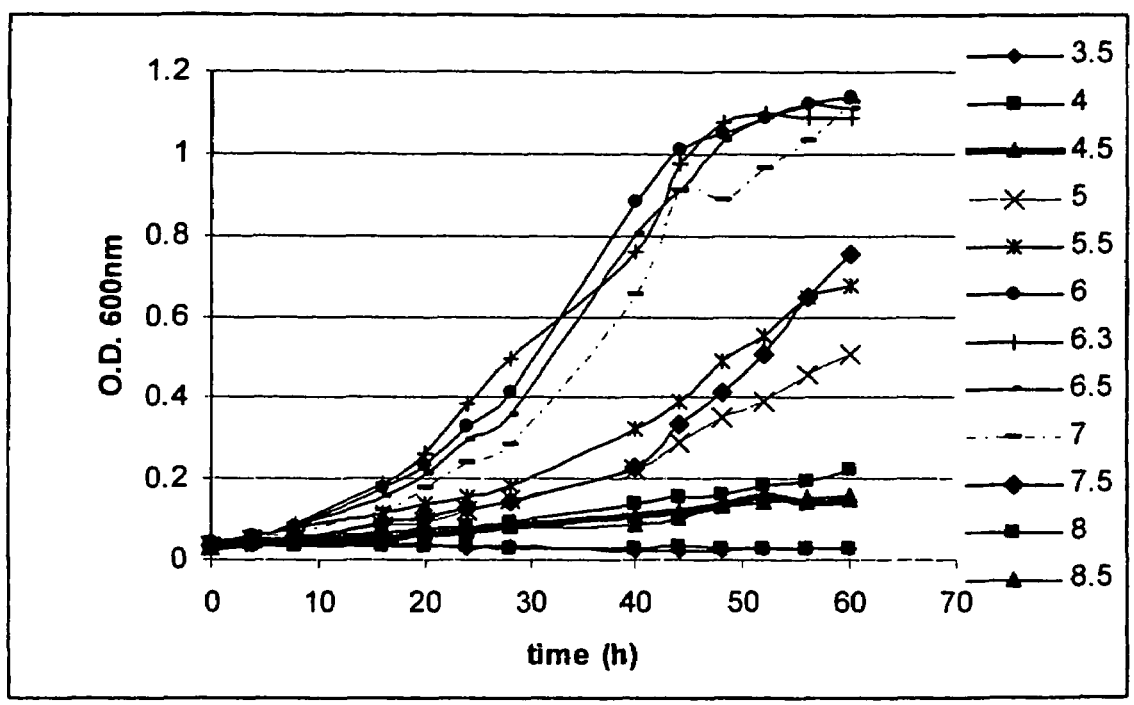
FIG. 2. Determination of optimum pH for strain P11 with fructose as the substrate.
Figure 3:
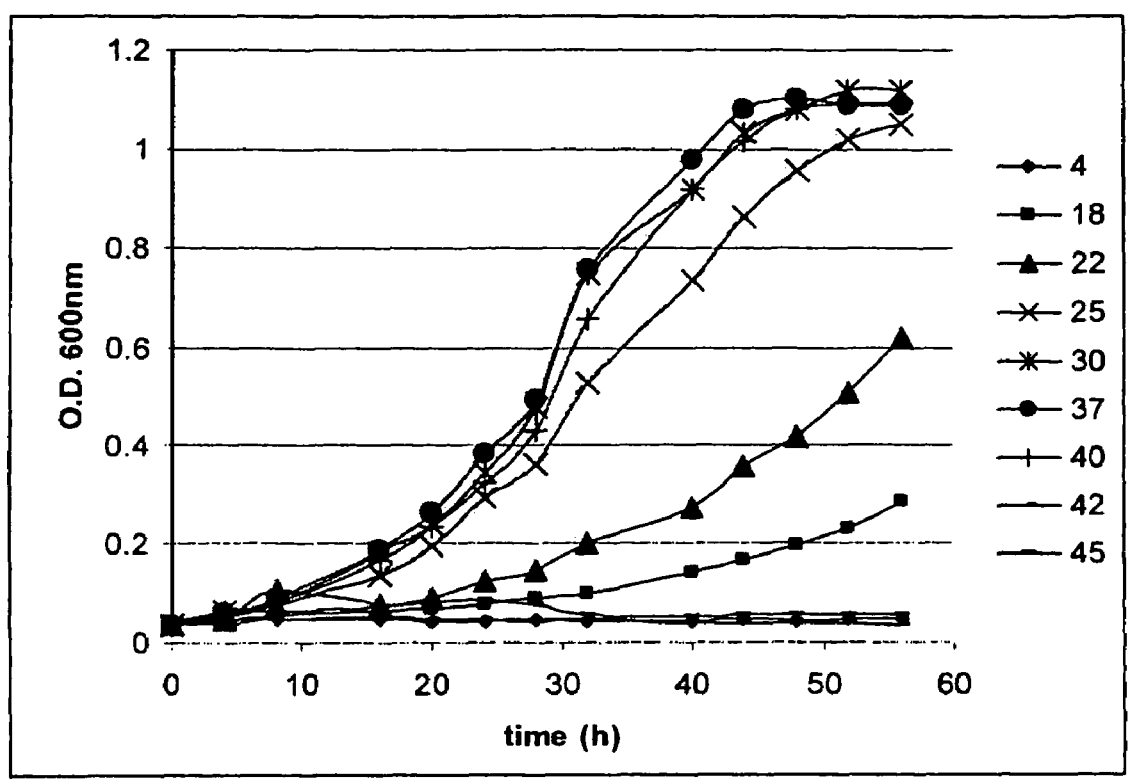
FIG. 3. Determination of optimum temperature for strain P11 with fructose as the substrate.
Figure 5:
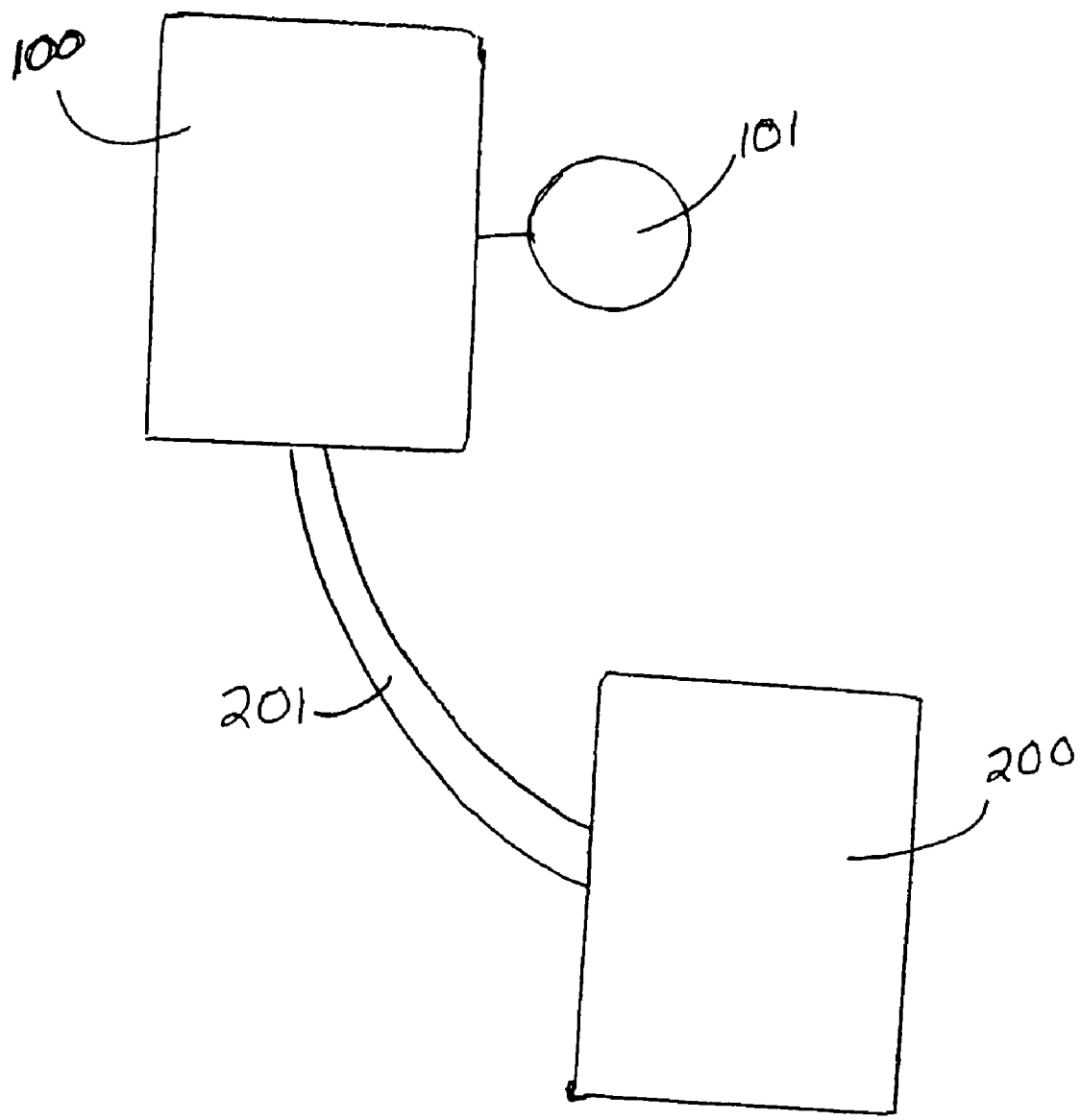
FIG. 5. Schematic for a system for producing ethanol from syngas using P11.

+, positive (indicates a final OD600 of greater than or equal to 0.1.)
−, negative (indicates a final OD600 less than the negative control.)
*result different from previously reported (Tanner, 1993).
†results of this study Strain P11 grew optimally at an initial pH 6.3; growth occurred at initial pH values between 4.0 and 8.5 (FIG. 2). When cultured in unbuffered media with an initial pH of 6.3, a final pH of 4.1 was measured. The optimal temperature for growth was 37° C. (FIG. 3); the temperature range in which P11 grew was 18-37° C.

The doubling time for strain P11 when grown with fructose and CO under optimal conditions was 0.143 h$^{-1}$ and 0.175 h$^{-1}$ respectively. However, when grown with xylose the doubling time decreased significantly (0.220 h$^{-1}$), indicating that xylose may be the preferred carbon and energy source of strain P11.

Strain P11 produced 2.35 mmol of acetic acid from 1 mmol of fructose; in addition, 0.63 mol of $CO_2$ and 0.5 mmol of ethanol were produced as end products (Table 7). Other acetogenic organisms, *Acetobacterium woodii*, *Acetobacterium wieringae* and *Acetobacterium carbinolicum* have also been observed to produce ethanol during the fermentation of hexoses (Buschhom et. al., 1989). Acetate was the only product formed in significant amounts when grown on $H_2/CO_2$, indicating that *C. ragsdalei* more than likely utilizes the acetyl coenzyme A (acetyl-Co-A) Wood/Ljungdahl pathway (Drake 1994).

TABLE 7

Fermentation balance of strain P11 with fructose.

| Substrate & Products | Yield mol/100 mol substrate | Carbon (mols) | O/R value | O/R value (mol/100 mol) | Available H | Available H (mol/100 mol) |
|---|---|---|---|---|---|---|
| Fructose | 100 | 600 | 0 | — | 24 | 2400 |
| Acetate | 222 | 444 | 0 | — | 8 | 1776 |
| $CO_2$ | 59 | 59 | +2 | +118 | 0 | 0 |
| Ethanol | 48 | 96 | −2 | −96 | 12 | 576 |
| Total | | 599 | 0 | +118, −96 | | 2400/2352 |

% carbon recovered, 99.8
% hydrogen recovered, 98
% oxygen recovered, 100

BOX-PCR genomic fingerprinting. The result of the gel electrophoresis of PCR products from *C. ljungdahlii* and strain P11 were compared (not shown). Both had a band of approximately 1,310 base pairs in size, a band of approximately 1,210 base pairs in size, a band of approximately 980 base pairs in size, a band of approximately 820 base pairs in size, a band of approximately 400 base pairs in size in common. *C. ljungdahlii* also had PCR product bands of 2,000 base pairs, 1,770 base pairs, 1,410 base pairs, 1,370 base pairs, 1,260 base pairs, 1,040 base pairs, 680 base pairs, and 360 base pairs in size. Strain P11 had unique band of 1,500 base pairs.

Therefore, these two clostridia were readily shown to be different using this technique. Although genomic fingerprinting is not a substitute for DNA-DNA hybridization, the use of this technique may be a valuable tool for many labs wanting to distinguish closely related bacterial strains.

Genetic analysis. Phylogenetic analysis of the 16S rDNA gene sequences of P11 indicated that the organism belonged to cluster I of the genus *Clostridium* (Collins et. al., 1994) essentially group I of Johnson & Francis (1975). In this cluster, strain P11 was located within a unit of five other clostridia; *C. ljungdahlii, C. tyrobutyricum, C. magnum, C. pasteurianum,* and *C. scatologenes*. The 16S rDNA sequence of strain P11 was most similar (99.9%) to that of *Clostridium ljungdahlii* ATCC M59097 (FIG. 4), an acetogen also capable of growth on CO (Tanner et. al., 1993).

Because of the high 16S rDNA similarity between strain P11 and *C. lungdahlii* a DNA-DNA hybridization study was performed. The determined value was 57 percent, clearly indicating that strain P11 was a novel species. The mol % G+C of the DNA was 29-30% (n=5), also similar to that of closely related *Clostridium* species.

This example shows that This example shows that *Clostridium ragsdalei* strain P11 is a distinct novel species, based both phenotypic differences to *C. ljungdahlii* and related species, and the clear standard of having less than 70% DNA-DNA relatedness (Wayne et al., 1987).

Example 2

The study of improving, maximizing or minimizing effects, and certain features already found to be contained within an organism without changing its inherent properties to obtain the most desirable result could be defined as optimization. Optimization studies are a key element in developing strategies to improve growth as well as the production of a desired fermentation product. In our case, ethanol is the desired end product.

Materials and Methods

Bacterial Strain and Cultivation Media. Clostridial strain P11 was used throughout the study. Carbon monoxide medium (COM) was used to cultivate and maintain the culture. The growth temperature was 37° C. COM is an undefined buffered medium initially pressurized to 10 psi (70 kPa) with $N_2/CO_2$ and then autoclaved for 15 minutes at 121° C. The medium contained per liter of distilled water: 25 ml mineral solution (Table 1), 10 ml trace metals solution (Table 2, 10 ml vitamin solution (Table 3), 1.0 g of yeast extract, 10 g of MES (2-[N-morpholino]ethanesulfonic acid), 0.001 g resazurin, 4.0 g cysteine.HCl, and 4.0 $Na_2S.9H_2O$; the initial pH of this medium was 6.1-6.3. The medium was prepared using strict anaerobic technique (Balch & Wolfe, 1976). Carbon monoxide was the sole substrate provided at 210 kPa (30 psi). Unless otherwise noted all growth experiments were conducted under a pressure of 30 psi with CO as the sole or primary substrate and were incubated horizontally to maximize gas diffusion into the medium. Standard inoculum size was about 2% (v/v) transferred from a stock culture that was growing in mid to late exponential phase, unless otherwise noted.

Analytical methods. Growth was measured spectrophotometrically at 600 nm (Spectronic 20D; Milton Roy) in aluminum seal tubes (Balch & Wolfe, 1976). Acetate and ethanol were measured simultaneously by a gas chromatograph (GC) equipped with a flame ionization detector (FID) on a Varian 3400 equipped with a 2 m steel column packed with an 80/120 Carbopak B-DA/4% carbowax resin 20M (Supelco, Bellfonte, Pa.). The column, injector, and detector temperature were 155, 200, and 200° C. respectively. Helium was the carrier gas and the flow rate was set at 30 ml $min^{-1}$. Hydrogen ion concentration was measured by electrode.

Metabolic Inhibitor Studies. Filter sterilized anaerobic stock solutions of fluoroacetate (FA) and trifluoroacetate (TFA) (Sigma Chemical Co.) were prepared to final concentrations of 4.5M. Before preparation, the FA and TFA powders were allowed to sit overnight in small beakers in the anaerobic chamber to allow any trapped oxygen to diffuse from the powder. Final concentrations ranging from 5 mM to 210 mM were assayed in trying to determine the minimum inhibitory concentration (MIC) and the most effective concentration to inhibit acetogenesis for maximum ethanol production relative to the growth yield. The inhibitors were usually added to the medium one day prior to inoculating with P11 to ensure anaerobicity was maintained. All additions were made anaerobically by syringe. During this study growth was measured periodically by spectroscopy. Toward the end of resting cell phase, liquid samples (1 mL) were taken and stored frozen (−20° C.) until analyzed by GC and HPLC.

Semi-Continuous Batch Cultures. Long term semi-continuous batch culture experiments were performed with 500 mL serum bottles containing between 100-200 mL of unamended COM. COM amended to a pH of 5.5 was also added for observation along with one culture grown in shaking conditions (50 rpm). The cultures were maintained by exchanging the spent liquid media with new unamended and amended COM and the addition/exchange of $H_2/CO_2$ to atmosphere and CO every 7-10 days. CO was added to at least 30 psi. During medium exchange growth and pH measurements were taken and liquid samples (1.0 mL) were taken from this and stored frozen (−20° C.) until ethanol and acetate were analyzed by GC and HPLC.

Ethanol tolerance. The effect of ethanol on CO metabolism and solvent production was investigated with strain P11. The initial maximum concentration at which strain P11 could survive was determined during the course of these studies. Balch tubes with COM containing ethanol concentrations ranging from 15-35 gram per liter were inoculated with P11 and growth was measured for approximately 10 days. Liquid samples (1.0 mL) were extracted once the cells remained at stationary phase and stored frozen (−20° C.) until analyzed by GC and HPLC. After the maximum ethanol concentration for cell survival was determined semi-continuous batch culture experiments were conducted using 500 mL serum bottles containing between 100-200 mL of COM containing different concentrations of ethanol (20, 30, 40, and 50 g/L) to adapt strain P11 to high solvent conditions. The amended COM with ethanol was prepared by adding filter sterilized ethanol to pre-sterilized Balch tubes, and then purging with N/CO2 to remove oxygen. After the media was sterilized, the ethanol was then added to the appropriate concentrations. These bottles were inoculated with the P11 cells from the semicontinuous batch cultures that were already established above. Growth and pH were measured periodically. A portion of the medium extracted for those measurements was taken for analyses of ethanol and acetate concentrations.

Trace metals. Iron (Fe), molybdenum (Mo), cobalt (Co), copper (Cu), and nickel (Ni) were examined at various concentrations to determine their effect on growth yield and ethanol production. Triplicate tubes of unamended (1×) and amended (0× and 10×) media were inoculated with strain P11 where each of these individual trace metals were added to or eliminated from the COM at 10× and 0× the original metal concentration. The cultures were fed every 48 hours with CO.

This was also completed in duplicate in 160 mL serum bottles to simulate small scale batch conditions. Stock solutions were prepared for each of the above metals and added during the media preparation before boiling and degassing. To minimize metal ion carry-over and deplete the amounts of the metals present in the cells for the 0 μM metals test concentrations, at least 6 transfers were made before the growth experiments were started. In order to adapt cells to the higher concentrations of metals, at least 2 transfers were made for each set-up. This experiment was performed in triplicate and growth was measured over 7 days after which pH and ethanol concentration analyses were completed.

Yeast extract. Various concentrations of yeast extract ranging from 0-2.0% were examined to determine their effect on growth and ethanol production. Growth was measured over a 7 day period and the pH and ethanol concentration determined at the conclusion of the experiment. Yeast extract was examined at the following percent concentrations: 0, 0.025, 0.05, 0.1, 0.2. CO was the primary substrate and carbon source. Strain P11 was adapted to the lower concentrations as before by using at least six consecutive transfers and at least two consecutive transfers for the higher concentrations.

pH. Optimum pH studies were completed to determine the best conditions for the enhancement of ethanol production from CO metabolism. For determination of the optimum pH, media was buffered with HOMOPIPES (homopiperazine-N, N'-bis-2-[ethanesulfonic acid] (Research Organics, Cleveland, Ohio), MES (2-[N-morpholino]ethanesulfonic acid), or TES (N-tris [hydroxymethyl]methyl-2-aminoethanesulfonic acid) at (1.0 g L-1). A 0.1 ml (~2%) inoculum of stationary phase CO grown cells was used to initiate growth. All media components used in these experiments were obtained from Sigma unless otherwise noted (Sigma Chemical Co., St. Louis, Mo.). At the completion of these experiments, pH was determined and the ethanol and acetate concentrations were analyzed.

Two sets of experiments were performed concerning pH. The first pH experiment was carried out in Balch tubes and growth was examined over 5 days without maintaining the pH. The second was carried out in small serum bottles (120 mL) to determine optimum pH for ethanol production. In the second setup the pH was controlled by the addition of sterilized 1N HCl or 1N NaOH.

Results

Metabolic Inhibitors—FA/TFA. The MIC established for fluoroacetate (FA) and trifluoroacetate (TFA) was 100 mM and 150 mM respectively. Definitive trends were not established with P11 for ethanol and acetate production in the presence of FA and TFA at the various concentrations assayed (see Table 8). When grown in COM containing 20 mM FA, no significant differences in growth yield (OD) and end products was observed relative to the P11 control. However, in the presence of 30 mM FA and above, acetate production decreased nearly ninety percent and the ethanol production and growth yield decreased fifty and forty percent respectively. The ethanol to acetate ratio increased eighty percent.

When grown in COM containing 30 mM TFA, there was a 126 and 52 percent increase in the ethanol and acetate produced respectively, although the solvent to acid ratio only increased slightly (50%). The growth yield remained unchanged. This suggests that carbon flow was shifted from acid to solvent production for both inhibitors used, only affecting the growth in the case of FA.

TABLE 8

Final OD and ETOH and acetate production with and without metabolic inhibitors

| End Product | P11 FA Control | P11 with 15 mM FA | P11 TFA Control | P11 with 60 mM TFA |
|---|---|---|---|---|
| Final OD 600 | 0.788 | 0.741 | 0.694 | 0.641 |
| Ethanol (mM) | 38.91 | 39.62 | 39.05 | 45.60 |
| Acetate (mM) | 445.86 | 48.72 | 45.18 | 34.58 |

Semicontinuous Batch Cultures

The P11 growth yield remained stable or increased during monitoring throughout a four month period. After correcting for dilution, the growth yield for one P11 culture reached 2.4 OD units. The pH for all cultures was consistently measured around 4.3. The amended COM (pH 5.5) achieved the highest ethanol yield at 252 mM (11.6 g/L) and ethanol to acetate ratio, whereas the highest unamended ethanol yield was 95 mM (4.4 g/L). An increase in acetate concentration and a decrease in ethanol production was the trend generally exhibited in cultures over the time period (a possible indicator of strain degeneration). The exception was the P11 culture initiated at a pH of 5.5. (Data is not shown.)

Ethanol Tolerance

Strain P11 was grown in COM amended with 15, 20, 25, 30, and 35 g/L and found to be initially tolerant of ethanol concentrations up to 30 g/L with the minimum inhibitory concentration being 35 g/L. Growth was retarded in the presence of all ethanol concentrations relative to the unamended control without ethanol. Measurable growth was not achieved for the amended cultures until 48 hours, except for the 25 g/L amended culture that grew at 98 hours (data not shown). The best growth at the highest ethanol concentration occurred at 20 g/L.

Using the culture growing the presence of the 20 g/L concentration and semi-continuous batch culture was started and maintained. Once the culture was established at 20 g/L an attempt to adapt it to 30 g/L was successfully made. This adaptation process continued until the 50 g/L concentration was reached. After this point, the culture was not able to be established at concentrations above 50 g/L although several attempts were made. Growth at the 50 g/L concentration was not able to be maintained above 0.55 OD units, but remained close to this level throughout the monitoring. Acetate and ethanol production had mixed results throughout the monitoring and therefore definitive trends were not established with these cultures.

Trace Metals

The effects of metal elimination and addition on CO metabolism in P11 were tested. The elimination of Fe, Co, Cu, and Ni limited CO metabolism. However, in the absence of Mo, CO metabolism increased slightly. The increased levels of Mo, Fe, Co, Cu, and Ni (200 μM, 80 μM, 12 μM, & 8 μM respectively) stimulated CO metabolism, and was especially noticeable after a 48 hour feeding (data not shown).

The solvent to acid ratio improved with the elimination of all metals, except Mo. In the case of Fe and Ni elimination, there was close to a 300 and 400 percent increase in the solvent to acid ratio. The elimination of Co and Cu decreased acetate production, increasing the solvent to acid ratio, while Mo elimination increased acetate production.

Yeast Extract

Initially strain P11 did not grow at the 0% yeast extract concentration and the growth experiment was only conducted with the other concentrations mentioned above. However, after nearly four weeks evidence of growth was observed. From that point on transfers were made every one to two weeks, and the initial tubes were refed with CO. At least 15 transfers were made. Thus, P11 can be adapted to grow in the absence of the complex medium component yeast extract.

Optimum pH Effects on Ethanol Production

Growth and alcohol:acid ratio was measured. The optimum pH for CO metabolism and ethanol production in *C. ragsdalei* was determined to be between 5.5 and 6.0. The ethanol:acetate ratio for the cultures with initial pH of 5.5 and 6.0 was 0.7:1 and 0.6:1 respectively.

Discussion

FA/TFA

Previously a 50 mM concentration of fluoroacetate had been shown to inhibit growth of a thermophilic clostridium (Rothstein, 1986). The importance of the data presented here is that it showed an increase of ethanol production by P11 in the presence of fluoroacetate and trifluoroacetate when compared to the control strains maintained in identical conditions.

Strain P11 was inhibited by ethanol at a concentration of 30 grams per liter upon initial isolation. Cultures were adapted to tolerate higher concentrations of ethanol by adaptation, similar to the adaptation techniques in Yamano et al., 1998. To date, the culture has been adapted to function fully at an ethanol concentration of 50 grams per liter ethanol. This example shows that adaptation procedures used in industrial microbiology can be used to enhance the performance of strain P11 as a microbial catalyst for ethanol and/or acetic acid production.

REFERENCES

Each of which is Incorporated Herein by Reference

Balch, W. E. & R. S. Wolfe. (1976). New approach to the cultivation of methanogenic bacteria: 2-mercaptoethanosulfonic acid (HS-CoM)-dependent growth of *Methanobacterium ruminantium* in a pressurized atmosphere. Appl Environ Microbiol 32, 781-791.

Bredwell, M. D., Srivastava, P., & Worden, R. M. (1999). Reactor design issues for synthesis-gas fermentations. Biotechnol Prog 15, 834-844.

Bryant, M. P. (1972). Commentary on the Hungate technique for culture of anaerobic bacteria. Am Journ Clin Nutrition 25, 1324-1328.

Buschhorn, H., Durre, P., & Gottschalk. (1989). Production and utilization of ethanol by the homoacetogen *Acetobacterium woodii*. Appl Environ Microbiol 55, 1835-1840.

Collins, M. D., Lawson, P. A., Willems, A., Cordoba, J. J., Fernandez-Garayzabal, J., Garcia, P., Cai, J., Hippe, H. & Farrow, J. A. E. (1994). The phylogeny of the genus *Clostridium*: proposal of five new genera and eleven new species combinations. Int J Syst Bacteriol 44, 812-826.

Drake, H. L. (1994). Acetogenesis, acetogenic bacteria, and the acetyl-CoA "Wood/Ljungdahl" pathway: past and current perspectives. In Acetogenesis, pp. 3-60. Edited by H. L. Drake. New York: Chapman and Hall.

Dubois, M., K. A. Gilles, J. K. Hamilton, P. A. Rebers, and F. Smith. 1956. Colorimetric method for determination of sugars and related substances. Anal. Chem. 28:350-356.

Johnson, J. L., & B. S. Francis. (1975). Taxonomy of the clostridia: ribosomal ribonucleic acid homologies among the species. J Gen Microbiol 88, 229-244.

Johnson, J. L. (1994). Similarity analysis of DNAs. In Methods for General and Molecular Microbiology, pp. 655-682. Edited by P. Gerhardt, R. G. E. Murray, W. A. Wood, and N. R. Krieg. Washington, D.C.: American Society for Microbiology.

Klass, Donald L. (1998). Biomass for renewable energy, fuels, and chemicals. San Diego, Calif.: Academic Press.

Licht, F. O. (2001). World Ethanol Markets, Analysis and Outlook. p. 17. Kent, United Kingdom: F. O. Licht Mesbah, M., Premachandran, U., & Whitman, W. B. (1989). Precise measurement of the G+C content of deoxyribonucleic acid by high-performance liquid chromatography. Int J Syst Bacteriol 39, 159-167.

Rothstein, D. M. 1986. *Clostridium thermosaccharolyticum* strain deficient in acetate production. J. Bacteriol. 165: 319-320.

Smibert, R. M., & Krieg, N. R. (1994). Phenotypic Characterization. In Methods for General and Molecular Microbiology, pp. 611-654. Edited by P. Gerhardt, R. G. E. Murray, W. A. Wood, and N. R. Krieg. Washington, D.C.: American Society for Microbiology.

Tanner, R. S., Miller, L. M., & Yang, D. (1993). *Clostridium ljungdahlii* sp. nov., an acetogenic species in clostridial rRNA homology group I. Int J Syst Bacteriol 43, 232-236.

Tanner, R. S. (2002). Cultivation of bacteria and fungi. In Manual of Environmental Microbiology, pp. 62-70. Edited by C. J. Hurst, Crawford, R. L., G. R. Knudson, M. J. McInerney, & L. D. Stetzenbach. Washington, D.C.: American Society for Microbiology.

Versalovic, J., Schneider, M., de Bruihn, F. J. & Lupski, J. R. (1994). Genomic fingerprinting of bacteria using repetitive sequence-based polymerase chain reaction. Methods Mol Cell Biol 5, 25-40.

Wayne, L. G., Brenner, D. J., Colwell, R. R., Grimont, P. A. D., Kandler, O., Krichevsky, M. I., Moore, L. H., Moore, W. E. C., Murray, R. G. E., Stackebrandt, E., Starr, M. P. & Trüper, H. G. (1987). Report of the ad hoc committee on reconciliation of approaches to bacterial systematics. Int J Syst Bacteriol 37, 463-464.

Yamano, L. P., S. W. York, and L. O. Ingram. 1998. Isolation and characterization of ethanol-tolerant mutants of *Escherichia coli* KO11 for fuel ethanol production. J. Indust. Microbiol. Biotechnol. 20:132-138.

Zeikus, J. G. (1980). Chemical and fuel production by anaerobic bacteria. Annu Rev Microbiol 34, 423-464.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A biologically pure culture of the microorganism *Clostridium ragsdalei* having all of the identifying characteristics of American Type Culture Collection No. PTA-7826.

2. A composition for producing ethanol, comprising a source of CO, and an effective amount of the *Clostridium ragsdalei* of claim 1.

3. The composition of claim 2, wherein said source of CO is syngas.

4. An apparatus for the production of ethanol, comprising in combination with a first a vessel provided with a source of CO and an effective amount of *Clostridium ragsdalei* having all the identifying characteristics of American Type Culture Collection No. PTA-7826; and a controller which controls conditions in said vessel for inducing said *Clostridium ragsdalei* to convert said CO to ethanol.

5. The apparatus of claim 4, further comprising a second vessel for producing syngas; and a transport system for transporting said syngas to said first vessel, wherein said syngas serves as said source of CO.

* * * * *

UNITED STATES PATENT AND TRADEMARK OFFICE
CERTIFICATE OF CORRECTION

PATENT NO.       : 7,704,723 B2
APPLICATION NO.  : 11/514385
DATED            : April 27, 2010
INVENTOR(S)      : Huhnke et al.

It is certified that error appears in the above-identified patent and that said Letters Patent is hereby corrected as shown below:

In column 2, line 55-59, delete

"*(Clostridium ragsdalei*, American Type Culture Collection Accession No. BAA-622, (now PTA-7826) deposited at the American Type Culture Collection located at 10801 University Blvd. in Manassas, Va., on October [provide calendar day] 2002, also referred to as 'P11')"

and insert

-- , namely *Clostridium ragsdalei*, first deposited as American Type Culture Collection Accession No. BAA-622 at the American Type Culture Collection (ATCC) located at 10801 University Blvd. in Manassas, VA, on October 16, 2002, and subsequently deposited at ATCC on June 14, 2006 in accordance with the provisions of the Budapest Treaty under Patent Deposit Designation PTA-7826, also referred to as "P11", --

Signed and Sealed this
Fifth Day of June, 2012

David J. Kappos
*Director of the United States Patent and Trademark Office*